United States Patent [19]

Isono

[11] Patent Number: 4,668,217
[45] Date of Patent: May 26, 1987

[54] CONNECTOR FOR THERAPEUTIC TUBING AND MEDICAL SOLUTION BAG DEVICE USING THE CONNECTOR

[75] Inventor: Keinosuke Isono, Kawaguchi, Japan

[73] Assignee: Terumo Kabushiki Kaisha, Tokyo, Japan

[21] Appl. No.: 785,024

[22] Filed: Oct. 4, 1985

Related U.S. Application Data

[63] Continuation of Ser. No. 727,618, Apr. 29, 1985, abandoned, which is a continuation of Ser. No. 647,262, Sep. 4, 1984, abandoned, which is a continuation of Ser. No. 390,628, Jun. 21, 1982, abandoned.

[30] Foreign Application Priority Data

Jun. 23, 1981 [JP] Japan .................... 56-95898
Dec. 25, 1981 [JP] Japan .................... 56-215398

[51] Int. Cl.⁴ ............................................ A61M 5/00
[52] U.S. Cl. .................................. 604/49; 604/280; 604/283; 604/29
[58] Field of Search ............... 604/280, 283, 905, 29, 604/86, 49-54

[56] References Cited

U.S. PATENT DOCUMENTS

| | | | |
|---|---|---|---|
| 3,332,418 | 7/1967 | Brody | 604/86 |
| 3,502,097 | 3/1970 | Muller | 604/280 |
| 4,019,512 | 4/1977 | Tenczar | 604/905 |
| 4,068,659 | 1/1978 | Moorehead | 604/280 |
| 4,270,534 | 6/1981 | Adams | 604/905 |
| 4,294,247 | 10/1981 | Carter et al. | 604/905 |
| 4,296,949 | 10/1981 | Muetterties et al. | 604/905 |
| 4,340,049 | 7/1982 | Munsch | 604/905 |
| 4,475,900 | 10/1984 | Popovich et al. | 604/905 |

FOREIGN PATENT DOCUMENTS

| | | | |
|---|---|---|---|
| 2486803 | 1/1982 | France | 604/905 |
| 1193759 | 6/1970 | United Kingdom | 604/283 |
| 2089921 | 6/1979 | United Kingdom | |

OTHER PUBLICATIONS

USA Standard-Dimensions of Glass and Metal Luer Tapers for Medical Applications, ANSI 8/1955.

Primary Examiner—C. Fred Rosenbaum
Assistant Examiner—Sherri E. Vinyard
Attorney, Agent, or Firm—Frishauf, Holtz, Goodman & Woodward

[57] ABSTRACT

A connector for therapeutic tubing comprising a tubular male connector member made of thermally resistant corrosionproof material, a tubular female connector member made of thermally resistant corrosionproof material and a locking mechanism coupled to the connector members and used for locking the union between the connector members. A medical solution bag device comprises a flexible bag, a flexible tube connected to the flexible bag, a further tube adapted be connected to the flexible tube and the above mentioned connector for connecting the flexible tube to the further tube.

12 Claims, 25 Drawing Figures

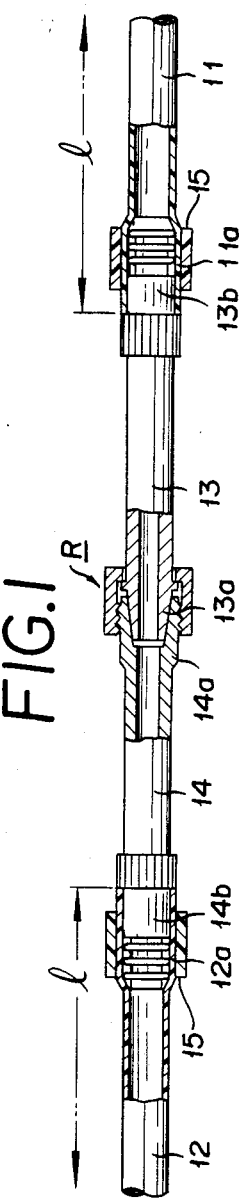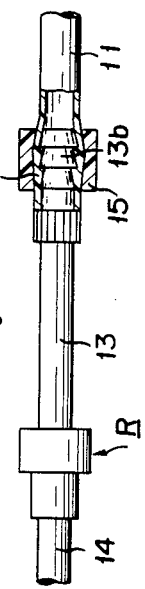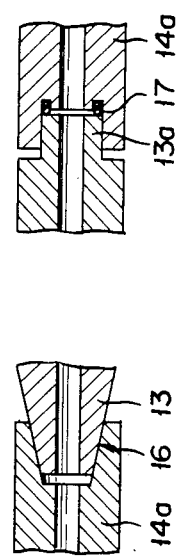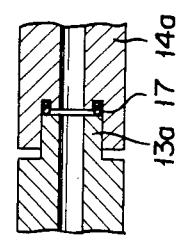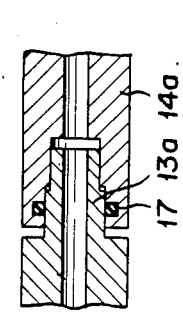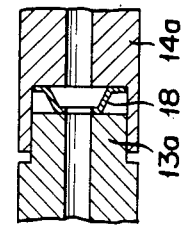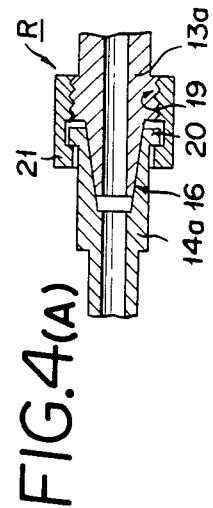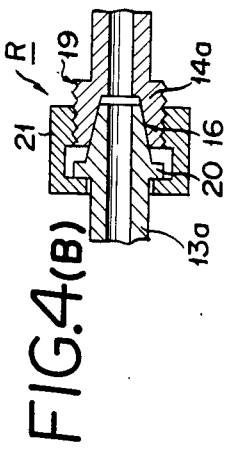

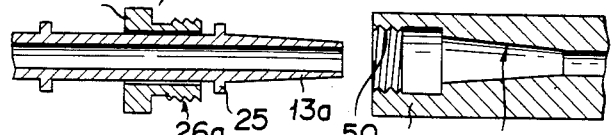
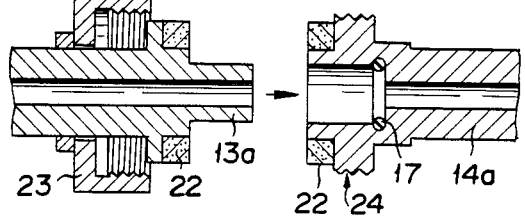
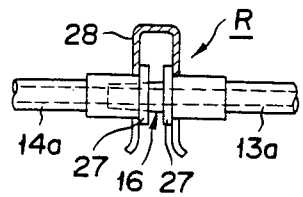
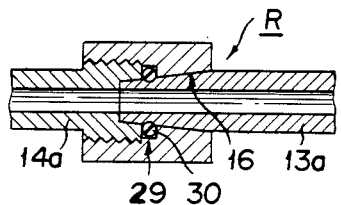
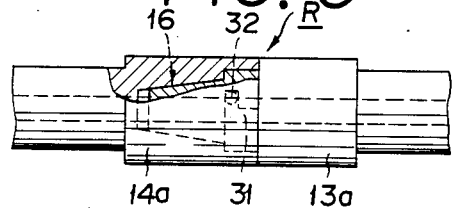
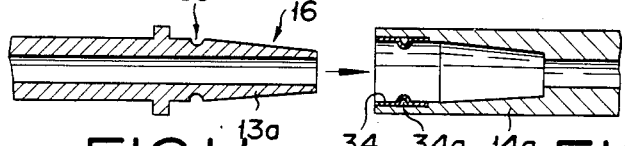
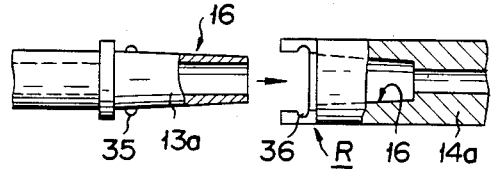
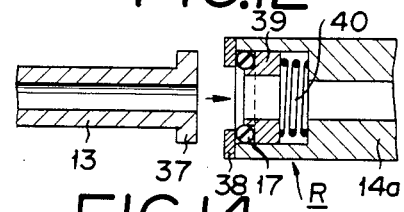
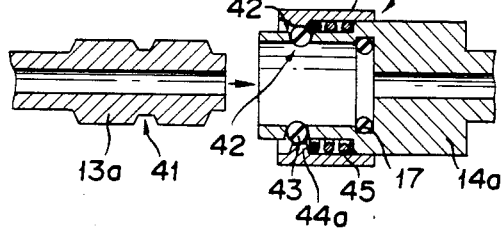
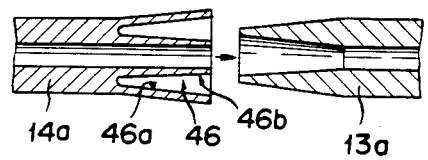

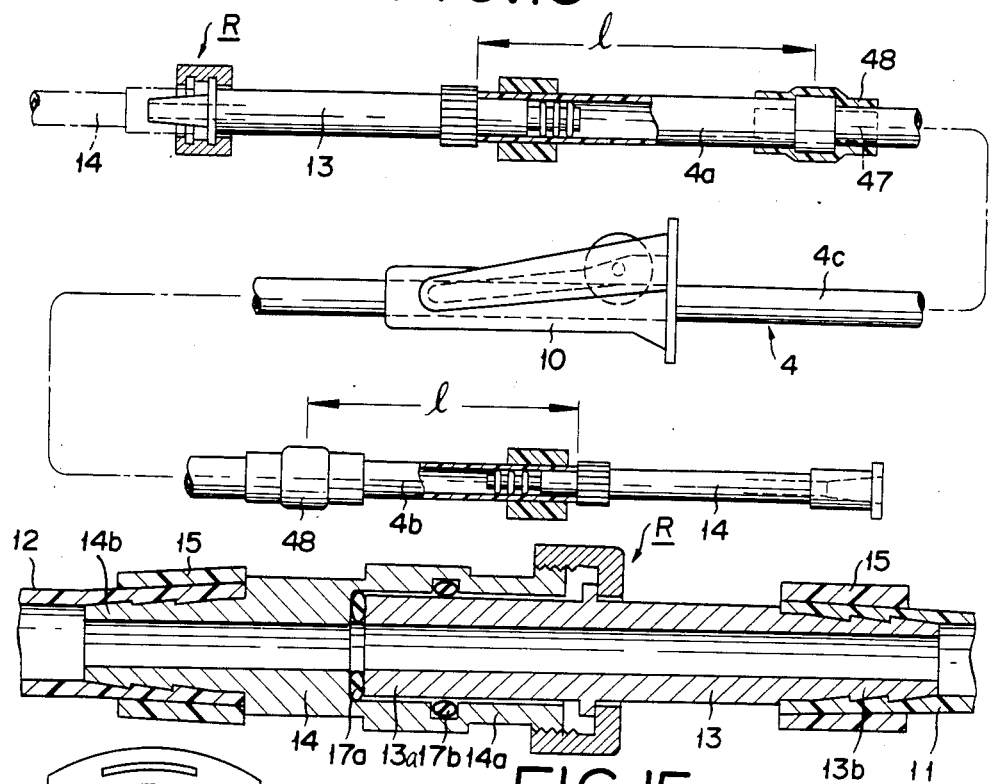
FIG. 16
FIG. 15
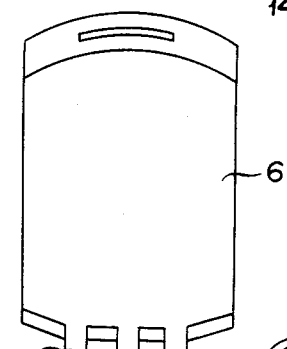
FIG. 17
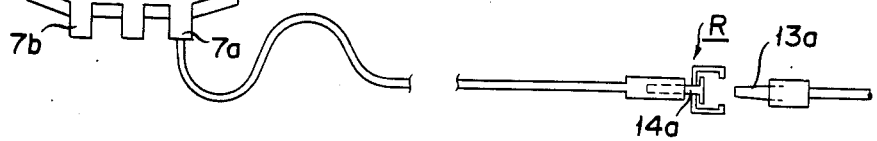
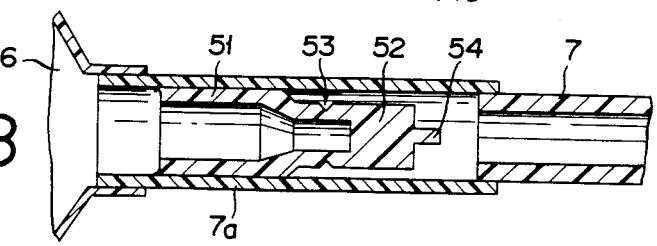
FIG. 18

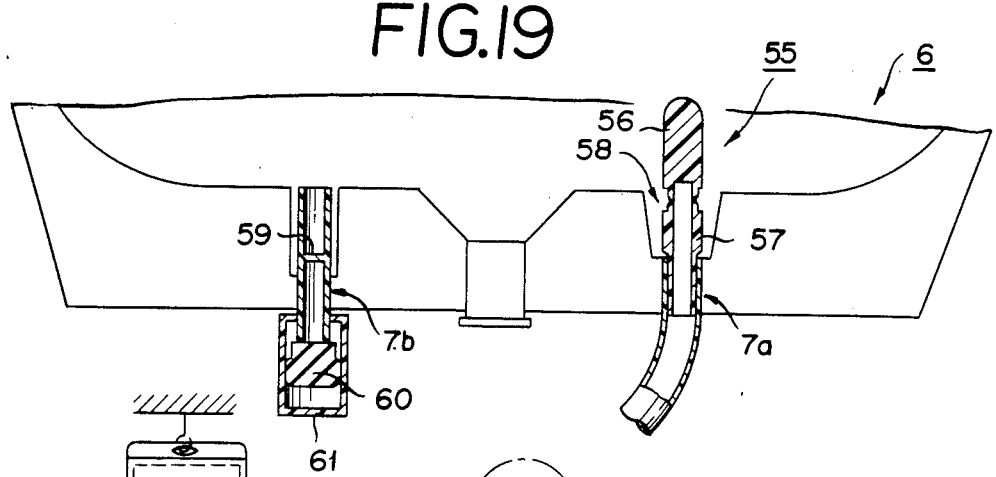
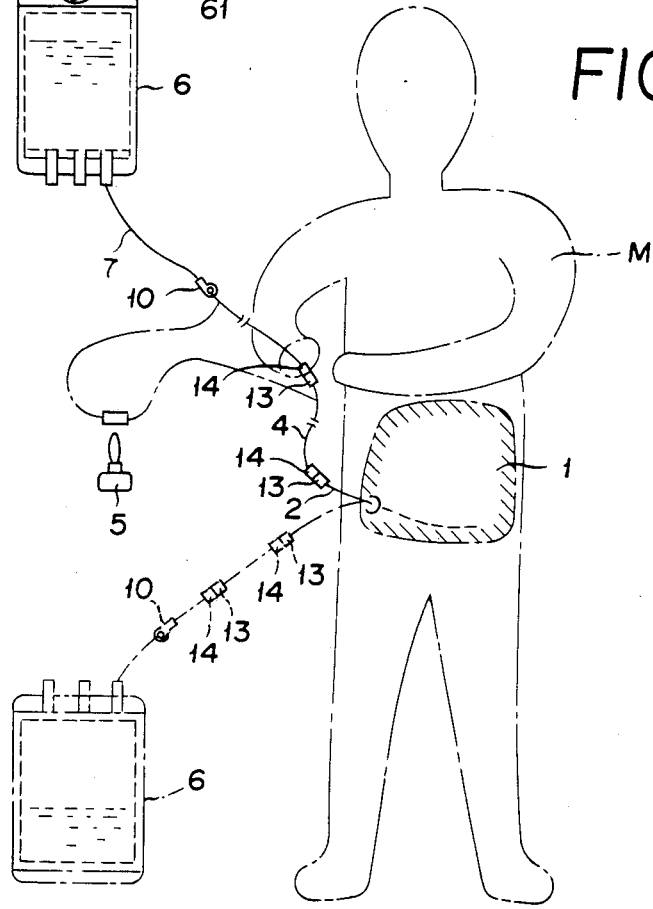

CONNECTOR FOR THERAPEUTIC TUBING AND MEDICAL SOLUTION BAG DEVICE USING THE CONNECTOR

This application is a continuation, Ser. No. 727,618, filed Apr. 29, 1985, which in turn is a continuation of Ser. No. 647,262, filed Sept. 4, 1984, which in turn is a continuation of Ser. No. 390,628 filed June 21, 1982 all now abandoned.

BACKGROUND OF THE INVENTION

1. Field of the Invention

This invention relates to a connector for therapeutic tubing and to a medical solution bag device using the connector. More particularly, this invention relates to a connector for therapeutic tubing used in dialysis and transfusion of solution and blood, which permits two tubes to be smoothly and easily connected with perfect water tightness and further enables the connected tubes to be unbreakably locked so that the tubes so connected and locked maybe a perfect barrier against invasion of microorganisms into the tubing no matter how often the tubes may have been separated and reconnected by this connector for continuous therapy over a long period and to a medical solution bag device, particularly transfusion bag means proper for peritoneal dialysis, using the connector.

2. Description of Prior Art

The tubing used for therapy by dialysis or transfusion of medicinal solution or blood is liable to be invaded by microorganisms when two tubes or one tube and a bag constituting the tubing are connected to each other. For the safety of the therapy, therefore, protection of the tubing against the microorganic invasion poses itself an important technical task. In the therapy by transfusion of blood, if microorganisms steal their way through a point of connection into the tubing and invade the blood vessels, the white blood corpuscles which have an ability to eat microorganisms will make the microorganic invasion scarcely menacing so long as the number of microorganisms participating in the invasion is small. In the therapy by dialysis, particularly peritoneal dialysis which is directed to the regions within the abdominal cavity which are totally destitute of defense against microorganic attacks, safe protection of the tubing used in the therapy against the microorganic invasion constitutes one absolutely essential technical task. The recent therapy by peritoneal dialysis is less complicated in mechanism and construction and notably less expensive than the conventional therapy by dialysis using an artificial kidney. The Medical science has substantially elucidated the causes for peritoneal adhesion. Thus, the therapy of the latest development is capable of effectively precluding the peritoneal adhesion and lightening the burden on the patient to a great extent. Besides, a system for continuous ambulatory peritoneal dialysis which enables the patient to engage normally in his daily work and, at the same time, receive continued therapy has been invented and adapted perfectly for practical use. Thus, the therapy by peritoneal dialysis has come to reawaken and arrest deep interest. The reliability of this particular method of dialysis regarding the safety of patient depends on the question as to whether or not the microorganic invasion of the tubing used in the dialysis can be perfectly prevented and, consequently, the plight of complicated peritonitis due to propagation of microorganisms within the peritoneum can be precluded. Unfortunately, it is held that the method of dialysis in its existing level is not capable of prolonged use.

The conventional method for continuous ambulatory peritoneal dialysis will be specifically described below. A catheter is surgically inserted into the abdominal cavity of a patient. A connector is attached to the external end of this catheter. With this connector, the other connector attached to the free end of a transfusion tube is coupled. Injection of a dialytic solution into the abdominal cavity is accomplished by hanging a bag containing the dialytic solution from a place higher than the abdominal cavity, piercing into the discharge port of the bag a bag syringe attached to the leading end of the transfusion tube, and loosening a clamp attached halfway along the length of the tube and fastened to plug or stop up the passage within the tube. After the injection of the dialytic solution into the abdominal cavity is completed, the aforementioned clamp is tightened on the tube and the tube is properly rolled into a coil, and the bag is stowed neatly at the waist of the patient. The patient is now free to walk around and engage in his normal work. After lapse of a stated length of time, the spent dialytic solution is withdrawn from the abdominal cavity. This withdrawal is effected by extending the tube, placing the bag on the floor, for example, and loosening the clamp on the tube. Then, the bag syringe is pulled out of the bag and the bag now containing the spent dialytic solution is discarded. The next dialysis is effected by setting a new bag containing a fresh supply of dialytic solution at a high level and then piercing the bag syringe into the transfusion port of the new bag. This procedure is repeated for the third and following cycles of dialysis.

At present, whenever the connectors are coupled and the bag syringe is inserted into the discharge port of the bag in preparation for the first cycle of dialysis and each of the following cycles of dialysis, disinfecting operates such as immersing the connectors momentarily in the solution of an iodine-based bactericide and thoroughly wiping the tip ofthe bag syringe with the bactericide are executed in order to prevent microorganic invasion of the tube interior. The bactericide in the solution enters the patient's body, though in a very small amount, and acts as a harmful substance. Thus, the bactericide is not allowed to be used in a high concentration but is required to be used in an extremely low concentration.

There has also been proposed equipment for continuous ambulatory peritoneal dialysis using a solution container connected by a flexible tube to a patient's tube leading into the patient's abdominal cavity, which equipment comprises a flexible, foldable plastic container for dialytic solution provided with a transfer port extended therefrom, a flexible tube extended from the aforementioned transfer port and provided at the leading end thereof with a luer connector for connection to a luer connector attached to the patient's tube, and a breakable member provided in the aforementioned flexible tube and adapted to obstruct the flow of the solution within the tube until it is broken (Japanese Publication of Unexamined Patent Application No. 55-99257, corresponding to United Kingdom Patent Application Nos. GB 2,040,379A and 2,063,684A). This equipment also requires the leading ends of the tubes to be immersed in the bactericide or wiped thoroughly with the bactericide before it is put to use. Therefore, this equipment has a similar disadvantage.

The disinfecting operation involved in the conventional devices, therefore, fall short of being justly called sterilization from the microorganic point of view. In fact, many cases of infection occur through connectors and bag syringes used after a lapse of about two months' time. In such cases, complication with peritonitis have been reported. At present, no effective measure is available for preventing this infection. Although the continuous ambulatory peritoneal dialysis proves to be a highly effective form of therapy as described above, it is held that this therapy cannot be safely performed for a long time.

OBJECTS OF THE INVENTION

It is, therefore, an object of this invention to provide a connector for therapeutic tubing, which can be heated with the flame of an alcohol lamp, for example, when it is connected, to ensure perfect sterilization and which neither generates rust nor causes undesirable changes of the surface owing to the heating.

Another object of this invention is to provide a connector for therapeutic tubing used in dialysis or transfusion of medicinal solution or blood, improved so that the connector can be safely held in bare hands while it is being heated for sterilization, the connector members when coupled with each other form a perfectly water tight bacteria barrier, the tubes joined to the connector members are prevented from being shrunk or expanded by the heat conducted through the connector members at the time the connector is heated, the water tight joint is continuously retained intact despite this heat, and the coupling of the connector members can be locked.

A further object of this invention is to provide a medicinal solution bag using the connector mentioned above.

This invention is aimed at providing a connector for tubing, which is advantageously used in the peritoneal dialysis necessitating countless repetitions of connection and disconnection over a long time and having no defense against microorganic attacks, particularly in the continuous ambulatory peritoneal dialysis requiring the patient himself to renew the dialysis at home and at work without the aid of his physician. The connector of this invention is not limited to the tubing used in dialysis. It is used equally effectively in the tubing to be used in the transfusion of medicinal solution or blood, wherein otherwise possible infection through the point of connection can be prevented with high reliability, when it is connected.

One supplemental object of this invention is to form the entire length of the tubing with flexible thermally resistant silicone resin (including silicone rubber, fluorine resin, etc. so that the tubing may be neither denatured nor deformed by the heat applied to the connector for the purpose of sterilization and the tubing may be fabricated by a smaller number of operation steps, or to form only an end portion of a required length of the tubing with the same silicone resin and the remainder of the tubing with less expensive polyvinyl chloride resin or polyethyelne so that the tubing may enjoy the same thermal resistance at a reduced cost. If the connector members are very bad heat conductors, there is no particular need for adoption of silicone resin.

Another supplemental object of this invention is to provide tubular support members to be wrapped fast around the connector members so that the connector members may be held in bare hands while the connector members are being heated for sterilization. In due consideration of strength, flexibility, and squeezing force peculiar to the particular material of the retaining members, the support members made of heat shrinkable silicone tubing are set in position so that they may fall on the outer face of the edge portions of tubing and squeeze the tubing against the a connector members. If such connector member is made of a material having lower thermal conductivity, such a tubular retaining member is not necessary.

Yet another supplemental object of this invention is to enable the connector members to be coupled through the union of diverging and converging tubular faces or the union of annular sealing members to ensure perfect water tightness of the joint.

A further supplemental object of this invention is to provide a varying locking mechanism which enables the joined tubing to be easily locked without imparting any twist to the tubing lest the union of the connector members should be accidentally disconnected to endanger the life of the patient.

SUMMARY OF THE INVENTION

The objects described above are accomplished by a connector for the therapeutic tubing, which comprises a tubular male connector member made of thermally resistant corrosionproof material, connected by insertion to the connecting end of one of the two tubes subjected to mutual connection, and possessed of a male engaging portion having an insertion edge shaped in a male form, a tubular female connector member made of thermally resistant corrosionproof material, connected by insertion to the connecting end of the other of the aforementioned two tubes subjected to mutual connection, and possessed of a female engaging portion having an insertion end shaped in a female form fit for fast insertion into the aforementioned male engaging portion, and a locking mechanism disposed to the two connector members and used for locking the union between the two connector members.

Further the objects described above are accomplished by a medicinal solution bag device, which comprises (A) a flexible bag proper possessed of at least one solution injection port, provided in a passage starting from the bag proper inside portion of the solution injection port and leading into the tubing connected to said port, with a passage means capable of obstructing the flow of solution from said bag proper before said bag means is put to use and releasing the obstruction of flow of the solution from said bag proper when said bag means is put to use, and containing the solution therein, (B) a flexible tube connected to the aforementioned solution injection port and adapted to guide the flow of the solution from or to the aforementioned bag proper, (C) a tube adapted to be connected to the aforementioned flexible tube, and (D) a connector for the therapeutic tubing comprising a tubular male connector member made of thermally resistant corrosionproof material, connected by insertion to the connecting end of one of the two aforementioned tubes subjected to mutual connection, and possessed of a male engaging portion having an insertion edge shaped in a male form, a tubular female connector member made of thermally resistant corrosionproof material, connected by insertion to the connection end of the other of the aforementioned two tubes subjected to mutual connection and possessed of a female engaging portion having an inserting end shaped in a female form fit for fast insertion into the aforementioned male engaging portion, and a locking mechanism disposed to the two connector members and used for locking the union between the two connector members.

BRIEF DESCRIPTION OF THE DRAWINGS

FIG. 1 is a front view illustrating, with portions sectioned for clarity, one typical connector for tubing according to the present invention.

FIG. 2 is front view illustrating, with portions sectioned for clarity, another typical connector.

FIG. 3 (A), (B), (C), and (D) are cross sections illustrating typical modifications to the water-tight connector according to the present invention.

FIGS. 4-15 are cross sections illustrating typical combinations of water-tight connectors and locking mechanisms used for locking the union of connector members.

FIG. 16 is a front view illustrating, with portions sectioned for clarity, an elongate tubing for continuous ambulatory peitoneal dialysis wherein the connector for tubing according to this invention is embodied.

FIG. 17 is a schematic diagram illustrating a typical medicinal solution bag means according to the present invention.

FIG. 18 is a cross section for illustrating the mechanism for establishing communication between the bag proper and the communicating tube in the medicinal solution bag means of this invention.

FIG. 19 is a cross section illustrating another embodiment of the communication mechanism.

FIG. 20 is a schematic diagram depicting a concept of the use of the medicinal solution bag means of this invention on a patient and FIG. 21 shows the method of connecting connector members according to the present invention.

DETAILED DESCRIPTION

Figure 21:
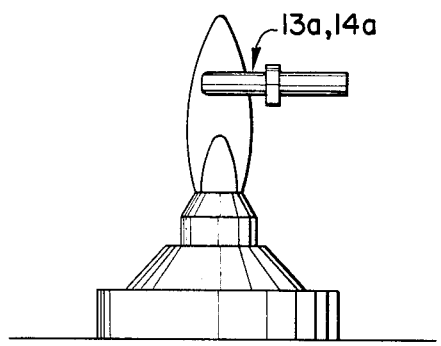

Now, preferred embodiments of this invention will be described below with reference to the accompanying drawings. As illustrated in FIG. 1, the connector of this invention for the therapeutic tubing such as is used in dialysis or transfusion of medicinal solution or blood is characterized by requiring one portion of tubes 11, 12 subjected to mutual connection, each of a stated length, l, from the connecting ends 11a, 12a thereof to be made of thermally resistant flexible material such as silicone resin, causing the outer surface of a short tubular male connector member 13 made of a thermally resistant corrosionproof material such as ceramics, stainless steel, titanium, titanium alloy or nickel plated brass, in a stated length, preferably 3 to 5 cm, connected to the connecting end 11a (12a) of one tube 11 (or 12) of the aforementioned two tubes, and having a male engaging portion 13a having an inserting end shaped in a male form to be connected by insertion to a tube connecting end 13b of a labyrinthal shape (or a shape having the diameter stepwise decreased in the direction of the end face), causing the tube connecting end 14b of a short tubular female connector member 14 made of a thermally resistant corrosionproof material such as ceramics, stainless steel, titanium, titanium alloy or nickel plated brass, in a stated length, preferably 3 to 5 cm, and having a female engaging portion 14a to be connected by insertion to the connecting end 12a (or 11a) of the other tube 12 (or 11), effecting union of the aforementioned male engaging portion 13a and the female engaging portion 14a by means of a suitable locking mechanism R capable of locking the union without imparting any helical driving motion to the connector members, and causing the portions of the aforementioned connector members 13, 14 approximately but not quite adjoining the respective tubes to be covered with tubular retaining members 15 made of a thermally insulating material such as heat shrinkable silicone tube, silicone resin (including silicone rubber), fluorine resin or cork. When the material of the connector members have low thermal conductivity, the tubular retaining members are not always required.

Examples of ceramics advantageously usable herein include zirconia, silicon nitride, alumina, silica, silicon carbide, steatite, and forsterite. Especially when zirconia is used, since it possesses high thermal resistance and a low thermal conduction coefficient, there is derived an advantage that the aforementioned limited portions of the tubes need not be made exclusively of the aforementioned thermally resistant flexible material but may be made of vinyl chloride resin, polyethylene, polypropylene or crosslinked ethylene-vinyl acetate copolymer and that the retaining member 15 is no longer required to be made exclusively of thermally insulating material.

The aforementioned tubes 11, 12 may be solely formed of silicone resin throughout their entire length. Otherwise, only stated lengths of the tubes from their connecting ends may be made of silicone resin and the remainders thereof made of soft, thermally nonresistant material such as vinyl chloride resin, polyethylene or polypropylene and the portions of different materials may be joined face to face to complete the tubes. When the material of the connector members have low thermal conductivity, the entire portion of the tube may be made of thermally nonresistant material. The retaining members 15 illustrated in FIG. 1 are formed of silicone resin. They are set around the tubes 11, 12 in advance. After the tubes 11, 12 have been forcibly wrapped around the engaging portions 13b, 14b respectively, the retaining members 15 on the tubes are shifted and forcibly over and around the outer face of the connecting ends of the tubes. When the retaining members 15 are made of fluorine resin which has virtually no flexibility as compared with silicone resin or cork which has poor tensile strength as illustrated in FIG. 2, they may be wrapped fast around the connector members 13, 14 or the connecting ends 11b (12b) of the tube 11 (12) are forcibly wrapped around the connector members 13, 14 with the aid of an adhesive agent.

For fast union of the aforementioned male and female connector members 13, 14 their respective male and female engaging portions 13a, 14a are only required to be so constructed that they come into water tight union when they are inserted straight one into the other. Desirably, the male and female engaging portions 13a, 14a may be shaped with perfectly matched converging and diverging tubular faces 16 which form a male and a female face capable of being coupled with each other with perfect water tightness as illustrated in FIG. 3(A). Optionally, a sealing member such as an O ring 17 or a countersunk packing 18 capable of being brought into intimate contact with the end face of, or being wrapped fast around the outer face of, the male engaging portion 12 may be set in position inside the female engaging portion 14a of the female connector member 14 as shown in FIGS. 3(B), (C) and (D).

FIGS. 4-15 represent various combinations of different forms of union established by insertion between connector members, which are essential components for the present invention, and different locking mechanisms capable of locking such union of connector members.

In FIGS. 4 (A) and (B), union of the male and female engaging portions 13a, 14a is obtained water tightly with their matched converging and diverging tubular faces 16. The locking mechanism R in this case is formed by cutting a thread 19 on the outer surface of either of the engaging portions 13a, 14a, providing a flange 20 on the remaining engaging portion 14a or 13a, and covering the flange 20 with a nut 21 helically matched to the aforementioned thread 19 so that the flange 20 may be pressed thereby against the other engaging portion 13a or 14a.

In the connector constructed as illustrated in FIG. 5, the water tight union is effected by means of an O ring 17. This union is locked by mutual attraction between magnetic rings 22, 22 attached fast to the end faces of the two engaging portions 13a, 14a and therefore opposed to each other and helical engagement between a nut 23 wrapped fast around the female engaging portion 13a and a screw 24 formed on the female engaging portion 14a.

In the construction of FIG. 6, the water tight union is effected by contact between matched and diverging tubular faces 16. The locking mechanism R in this case comprises a flange 25 formed on the outer surface of the male engaging portion 13a of the male connector member, a clamping nut 26 provided with a male screw 26a and rotatably set around the male engaging member 13a opposite the side for connection with the connector member across the flange 25 and the tube, and a female screw 50 formed inside the female engaging portion 14a of the female connector member and adapted to fit helically into the aforementioned male screw 26a.

In the construction of FIG. 7, the water tight union is effected by insertion of matched converging and diverging tubular faces 16 one into the other. The locking mechanism R in this case is provided with flanges 27, 27 formed on the two engaging portions 13a, 14a respectively and a lock pin 28 of a special shape such that it can be set astride the two connector members perpendicular to the direction of the union and consequently can be brought into intimate contact with the opposite faces of the paired flanges 27, 27.

In the construction of FIG. 8, the water tight union is effected by means of matched converging and diverging tubular faces 16. The locking mechanism R in this case comprises an annular groove 29 formed in the circumferential direction on the outer surface of the male engaging portion 13a and an O ring 30 made preferably of metal adapted to snap into locked engagement with the aforementioned groove 29, and received unretractably in the female engaging portion 14.

In the construction of FIG. 9, the water tight union is effected by mean of matched converging and diverging tubular faces 16. The locking mechanism R in this case comprises an L-shaped slit 31 cut on the outer surface or the inner surface inwardly from the end face into the female engaging portion 14a of the female connector member and a protuberance 32 formed on the outer surface of the male engaging portion 13a of the male connector member and adapted to advance through the axial portion of the L path of the aforementioned slit 31 and to come into locked engagement with the bent portion of the L path.

In the construction of FIG. 10, the water tight union is effected by means of a converging tubular face 16 and a matched diverging tubular face. The locking mechanism R in this case comprises an annular groove 33 formed in the circumferential direction on the outer surface of the male engaging portion 13a of the male connector member and a leaf spring 34 provided with a protuberance 34a adapted to drop into locked engagement with the annular groove 33 upon completion of the union and attached fast to the inner surface of the female engaging portion 14a of the female connector.

In the construction of FIG. 11, the water tight union is effected by matched male and female tapered tubular faces 16. The locking mechanism R in this case comprises a protuberance 35 formed on the outer surface of the male engaging portion 13a of the male connector member and a recession 36 adapted to receive the aforementioned protuberance 35 into locked engagement and formed on the inner surface of the female engaging portion 14a of the female connector member.

In the construction of FIG. 12, the water tight union is effected by means of an O ring 17. The locking mechanism R in this case comprises a flat flange 37 formed on the outer surface of the male engaging portion 13a of the male connector member, a recess formed in the female engaging portion 14a of the female connector member so as to admit entry of the aforementioned flange 37, and a departure-preventing plate 38 disposed in the end face of the female engaging portion 14a of the female connector member and provided with a passage (not shown) cut to permit selective entry and departure of the flange 37 into and from the female engaging portion 14a depending on the positional relation in the circumferential direction of the projection of the flange 37. The aforementioned O ring is kept amply in intimate contact on the entire circumference thereof with the inner surface of the female engaging portion 14a by a retainer ring 39, held in position as carried slidably in the direction of insertion, and energized by a coil spring 40 to remain in contact with the inner surface of the aforementioned departure-preventing plate 38. Owing to the arrangement described above, the end face of the male engaging portion 13a comes into water-tight contact with the packing 17 and the peripheral surface of the flange 37 comes into secure engagement with the inner surface of the recess of the female engaging portion 14a when the male engaging portion 13a of the male connector member is pushed into the female engaging portion 14a of the female connector member and then slightly twisted.

In the construction of FIG. 13, the water tight union is effected by means of an O ring 17. The locking mechanism R in this case comprises an annular groove 41 formed in the circumferential direction on the outer surface of the male engaging portion 13a of the male connector member, a conical hole 42 perforated in the shell of the female engaging portion 14a of the female connector member, a ball 43 thrust inwardly from the bottom of the conical hole 42 so as to come into engagement with the aforementioned groove 41, a lock ring 44 formed as provided on the inner side thereof with a wedge claw 44a capable of pressing the ball 43 in the direction of the bottom of the conical hole 42 and wrapped around the female engaging portion so as to conceal the ball 43, and a coil spring 45 stowed on the inner side of the lock ring 44 and adapted to energize the lock ring 44 in the direction of the end face of insertion and cause the claw 44a to press the ball 43 against the bottom of the conical hole 42. The water tight union of the connector members and the locking of this union are simultaneously effected by sliding the lock ring 44, then inserting the male engaging portion 13a into the female engaging portion 14a, and letting the lock ring 44 snap into position.

In the construction of FIG. 14, the water tight union and the locking of this union are effected at the same time. The locking mechanism R in this case comprises an annular groove 46 formed inwardly from the end face of the female engaging portion 14a of the female connector member in the axial direction of a thick-walled inner coupling, the annular groove 46 being defined by a female tapered tubular face 46b and a female tapered tubular face 46a of a larger diameter than the female tapered tubular face 46b thereby assuming the shape of a wedge having a cross section gradually decreasing in thickness toward the recess, and a tapered tubular wall formed of part of the male engaging portion 13a of the male connector member with the inner and outer surfaces thereof matched to the aforementioned tapered tubular faces 46a, 46b so as to fit the tapered tubular wall 13a for insertion into fast engagement with the aforementioned groove 46.

FIG. 15 illustrates another embodiment of the present invention, which is constructed with a female connector member 14 made of a low thermal conductive material such as ceramic, titanium, titanium alloy and nickel plated brass, provided with O rings 17a, 17b in a hole of the end 14a, and a male connector member 13 made of similar material inserted into the hole at the end 13a, locked by a locking mechanism R. At other ends 13b, 14b of each connector members, usual tubes 11, 12 such as vinyl chloride resin tubes are connected, and further is covered with a retaining members 15 such as heat shrinkable silicone tube.

FIG. 16 represents a typical elongate tubing for continuous ambulatory peritoneal dialysis wherein the connector for tubing according to this invention is embodied. This elongate tubing 4 is provided at the opposite ends thereof with a male connector member 13 and a female connector member 14. The end portions, each of a stated length l, of the elongate tubing 4 adjoining the connectors 13, 14 form tubes 4a, 4b each made of silicone resin. The remainder of the tubing 4 is a tube 4c made of flexible vinyl chloride resin. The joining of the tube 4a or 4b to the tube 4c is effected by having the opposed ends of the tubes fitted around a short rigid coupling tube 47 having the middle portion of its outer surface formed in an increased diameter, then moving a thermally shrinkable sealing tube 48 fitted in advance around either of the tubes until it completely conceals the joined ends of the tubes, and causing the tube 48 to shrink by application of heat. The tube 4c has a flow clamp 10 fitted around itself. The connector members 13, 14 may have supporting members 15, 15 forcibly wrapped around the tubes 4a, 4b respectively. They are further provided with nuts adapted to serve as a locking mechanism R. For effective service of the enlongate tubing 4, it is only natural that a connector member attached to the patient's tubing should be provided with a corresponding male engagng portion or female engaging portion adapted to be connected to the elongate tubing.

Now, a typical medical solution bag device using the connector of the present invention will be described below. As illustrated in FIG. 17, the medical solution bag device is provided with a bag proper 6. This bag proper is made of a material which is pliable and capable of withstanding the conditions of sterilization in an autoclave. Examples of the material satisfying this requirement are flexible vinyl chloride resin, crosslinked polyethylene-vinyl acetate copolymer, polypropylene, polycarbonate, polyamide, polyethyelene terephthalate, and polybutylene terephthalate. This bag proper 6 is provided with a solution injection port 7a formed of a short tube and optionally with a solution mixing port 7b formed similarly of a short tube.

The solution injection port 7a is provided with a flow tube 7 adapted to guide the outward flow of the solution from the bag proper 6 (such as medicinal solution or blood) and made of a material pliable and capable of withstanding the conditions of sterilization in an autoclave (similar to the material used in the bag proper). Optionally the flow tube 7 may be provided with a passage mechanism which blocks the passage leading into the bag proper 6 and obstructs the flow of the solution from the bag proper 6 before the bag device is put to use and which opens up the passage and aids in the flow of the solution from the bag proper 6 when the bag device is put to use. This passage mechanism may be formed in any desired construction on condition that the construction permits the mechanism to fulfill its function to advantage. For example, it may be formed by providing the solution injection port 7a or the flow tube 7 with a pierceable partition wall (not shown) and having a hollow piercing member kept within the solubtion injection port 7a. In this arrangement, desired passage is effected by causing the hollow piercing member to pierce through the partition wall and establish communication between the bag proper 6 and the flow tube 7.

A passage mechanism illustrated in FIG. 18 comprises a hollow tube 51 made of a rigid plastic substance such as, for example, rigid vinyl chloride resin in a construction having an outside diameter substantially equalling the inside diameter of the solution injection port 7a and a leading end converged in the forward direction and a solid cylinder 52 continuously extended from the leading end of the hollow tube 51 in a diameter smaller than the inside diameter of the solution injection tube and larger than the inside diameter of the flow tube 7. This passage mechanism is attached fast to the inner wall of the solution injection tube 79. The flow tube 7 is set fast in position within the solution injection port 7a. On the hollow tube 51 and close to the boundary between the hollow tube 51 and the solid cylinder 52, there is provided an annular notch 53. Before the bag device is put to use, the solid cylinder 52 obstructs the passage between the bag proper 6 and the flow tube 7. When the bag device is put to use, the solid cylinder 52 is severed along the annular notch 53 by pressure exerted externally with the finger tip, for example, so as to establish communication between the bag proper 6 and the flow tube 7 via the interior of the hollow tube 51, with the result that the solution from the bag proper 6 is allowed to flow through the interior of the flow tube 7. From the end face of the solid cylinder, a protuberance 54 of a shape of a flat plate having a width equalling the diameter of the cylinder 52 is extended. This protuberance 54 serves the purpose of preventing the severed solid cylinder 52 from occuluding the flow tube 7.

As illustrated in FIG. 18, the flow tube 7 is provided at the foremost end thereof with the aforementioned connector members 13a, 14a and the linking mechanism R which will be connected to a catheter (not shown) leading into the patient's abdominal cavity. The aforementioned passage means may be disposed either halfway in the whole length of the flow tube 7 or at the end of the solution injection port 7a falling inside the bag proper 6.

FIG. 19 illustrates another embodiment of the present invention. A passage mechanism 55 adapted to obstruct the outward flow of the solution from the bag proper 6 while the bag means is not in use and guide the flow of the solution while the bag means is put to use, is provided at the end of the solution injection port 7a falling inside the bag proper 6. In addition, a solution mixing port 7b is disposed as illustrated. The passage mechanism 55 comprises a solid cylindrical member 56 and a tubular member 57 which continue into each other across a common end and are made of a rigid plastic such as, for example, rigid vinyl chloride resin in an outside diameter substantially equalling the inside diameter of the solution injection port 7a with an annular notch 58 formed near the boundary between the solid cylindrical member 56 and the tubular member 57. Before the bag means is put to use, therefore, the flow of the solution from the bag proper is obstructed by this solid cylindrical member 56. At the time that the bag means is put to use, the solid cylindrical member 56 is severed along the annular notch 58 by pressure exerted thereon with the finger tip, for example, so that communication may be established between the interior of the bag proper 6 and the flow tube 7.

The solution mixing port 7b has the internal cavity thereof divided by a partition wall 59 halfway along its entire length. It is further provided at the leading end thereof with a rubber member enclosed with a cover 61. Desired injection of a necessary medicine into the bag proper is accomplished by piercing a needle of the syringe through the cover 61 and the aforementioned partition wall 59. After the needle has been withdrawn from the partition wall, possible backflow of the solution from the bag proper is obstructed by the rubber member 60.

Now, embodiments of the connector and the medicinal solution bag means of this invention used for continuous ambulatory peritoneal dialysis (CAPD) will be described. As illustrated in FIG. 20, a catheter 2 is surgically inserted into the abdominal cavity 1 of a patient and the connector member 13 is attached to the end of the catheter 2. The tubing 4 which has connector members 14, 13 sterilized previously and covered with a protecting cap fastened one each at the opposite ends thereof is connected to the catheter 2, after removing the protecting cap, by causing the connector member 14 of the tubing 4 and the connector member 13 of the catheter 2 to be coupled with each other after they have been sterilized with the flame of an alcohol lamp, for example. Similarly, the connector member 14 sterilized previously and covered with a protecting cap, attached to one end of the flow tube 7 led into the solution injection port 7a of the bag proper and the connector member 13 of the tubing 4 are coupled with each other after removing the protecting cover and after they have been sterilized with the same flame. Subsequently, the bag proper 6 is hung down at a level higher than the abdominal cavity and the cylindrical member 52 or 56 in the passage mechanism is bent and broken along the annular notch 53 or 58 to establish communication between the interior of the bag proper and the flow tube 7. Injection of the dialytic solution into the abdominal cavity is is started by loosening the clamp 10. On completion of the injection, the clamp is refastened, the tubing is properly rolled into a coil, and the bag proper 6 is stowed at the waist. Consequently, the patient is now free to walk around and engage in his normal work. Withdrawal of the spent dialytic solution from the abdominal cavity 1 after lapse of a stated length of time is effected by stretching out the tube 7, placing the bag proper 6 on the floor, for example, and loosening the clamp 10. Then the connector members 13, 14 kept in union so far are separated from each other while they are sterilized with the flame. The bag proper now containing the spent dialytic solution is replaced with a new bag proper 6 containing a fresh supply of dialytic solution. This embodiment represents a case wherein connectors for tubing according to the present invention are disposed one each at two points. This embodiment offers a conspicuous advantage in that the tubing 4 interposed between the two connectors can be made disposable when trouble occurs during the insertion for a long time. The connectors for tubing according to the present invention may be used one each at three or more points such as in the system for continuous ambulatory peritoneal dialysis. The tube 4 is sometimes inserted for a long time, so it is desirable to adopt a silicone tube so as not to attach an alien substance to an inner wall of the tube.

Now, the operation for effecting the union by the connector of the present invention will be described below with reference to FIG. 20 and 21. It is assumed that the tube 11 corresponds to the elongate tube 4 connected to the catheter implanted in the patient's abdominal cavity and the tube 12 to the flow tube 7 connected to the bag. To renew dialysis, since the bag and the flow tube 12 are disposable, the locking mechanism R is released and the engagement between the male engaging portion 13a and the female engaging portion 14a is broken. Preparatory to breakage of the engagement, the patient is required to hang a new bag from a high level, sterilize a new flow tube 12 and connect it to the bag, take hold of the retaining member 15 on the previously sterilized female connector member 14 at the leading end of the flow tube 12 in one of his own hands, remove a cap for maintaining sterilization (not shown) and heat the female engaging portion 14a properly with the flame of an alcohol lamp as shown in FIG. 2, get hold of the retaining member 15 of the tube 11 still connected as described above either in the other empty hand or in both hands holding a new spare and release the engagement between the male connecting portion 13a of the flow tube 12 with the female connecting portion 14a directly above the flame of the alcohol lamp and, immediately heat the male engaging portion 13a of the male connector member 13 connected to the tube 11 properly with the flame of the alcohol lamp as shown in FIG. 21 and insert the sterilized male engaging portion 13a into union with the female engaging portion 14a of the female connector member 14 connected to the flow tube 12, and lock the union of the connector members 13, 14 again with the locking mechanism R. In this manner, otherwise possible entry of microorganisms into the tube can be perfectly prevented and, consequently, possible complication of peritonitis due to invasion of microorganisms through the joining of connector members can be completely eliminated. Since the connector members 13, 14 are resistant to heat and corrosion proof, they neither gather rust nor undergo undesirable change on the surface when they are heated. When the engaging portions 13a, 14a of the connector members 13, 14 are heated with the flame of the alcohol lamp, the tube side ends of the connector members 13, 14 become hot, if the connector members have high thermal conductivity. Since these portions are covered with the retaining members 15, the patient can safely hold the connector members 13, 14. Further, since the supporting members 15 have a large diameter and the retaining member enhances the engagement of the tube with the connector, the patient can hold them comfortably and steadily to effect the heating advantageously. When the corresponding portions of the tubes 11, 12 are made of silicone resin, there is no possibility that the tubes will be contracted, expanded, embrittled, or melted by the heat conducted through the connector members 13, 14. Thus, the dialytic solution will not leak through the joints between the tubes and the connector members. The connection of tubing involving the sterilization with the heat from the flame, therefore, can be advantageously effected without any adverse effect on the tubing. It is desirable that the female connector member is provided with an end of the flexible tube connected to the bag and the male connector member is provided with the tube to be connected. That is to say, the connector member of the end of the tube at the side of the patient is used for several times, so it is desirable to be the male connector member which is easy and secured to flame sterilization.

This invention is constructed as described above, A medical treatment by use of equipment incorporating the connectors of this invention, therefore, can be carried out without fear of bacterial infection.

In the course of a medical treatment, using the invention perfect sterilization can be maintained by heating the relevant engaging portions of connector members by the flame of an alcohol lamp when an existing union of two connector members is broken and the connector member of a new tube and the connector member of the continously used tube are joined for renewal of treatment or when a cap placed on the stopper of the connector member of the elongate tube currently in use is removed and the freshly opened connector member is joined to the connector member of the flow tube and, afterward, this union is broken and the cap is replaced on the connector member to permit one cycle of treatment. Particularly, when the medical treatment involves those organs of the body absolutely defenseless against bacterial attacks such as in peritoneal dialysis, the equipment mentioned above completely precludes the possible complication of peritonitus due to the leakage of microorganisms through the joining of connector members. In a wide range of medical treatments, therefore, adoption of the connector for tubing according to this invention notably heightens the reliability of equipment with respect to the safety of life.

Various conventional medical treatments involving use of catheters and consequently necessitating use of tubings and attendant connector members as in peritoneal dialysis, for example, have had a serious disadvantage in that they cannot be safely performed for a long time because they are unable to preclude entry of microorganisms through the joining of connector members. The equipment using the connectors of this invention has an outstanding effect of completely overcoming this disadvantage. Moreover, in accordance with this invention, union of connector members and breakage of this union can be carried out very easily in one hand by the patient unaided by a physician without jeopardizing perfection of the sterilization state. The connector for tubing according to this invention, therefore, proves to be ideal for use in the equipment for continuous ambulatory peritoneal dialysis.

Further, by the connector members in the connector of this invention being exclusively made of thermally resistant corrosionproof material such as ceramics, stainless steel, titanium, titanium alloy or nickel plated brass, they endure prolonged use because they undergo neither chemical change nor deformation when they are directly exposed to an open flame of an alcohol lamp. Thus, they enjoy high reliability of mechanical performance. The portions of the tubing which adjoin the connector members are made of a heat resistant material such as silicone resin, etc. and, therefore, can be forcibly joined with the connector members with ample strength. They are not shrunk, expanded, melted, or softened by the heat conducted through the connector members during the sterilization. The connector of this invention, therefore, brings about an advantage that the liquid tight joints between the connector members and the tubes can be retained safely.

Further, in accordance with this invention, when the connector members are each provided with retaining members made of heat resistant material, it is possible to use if the material having high heat conductivity is used. The connector members in the connector of this invention are designed to be joined through insertion one into the other. The union of such connector members and the subsequent locking of this union, therefore, can be effected smoothly in one hand by the patient himself. In accordance with this invention, the connector members are designed to be joined by insertion, and union by means of threads is adopted optionally in the locking mechanism. The union of the connector members, therefore, can be effected very smoothly without imparting any twist to the tubes. Thus, there is no possibility that a twist imparted to the tubes will give rise to a moment tending to rotate the tubes in the direction of undoing the twist and, consequently, the locking mechanism will be spontaneously disposed to release itself. This is utterly inconceivable in the case of this invention. Also in this respect, the connector of the present invention ought to prove to be ideal for the equipment for continuous ambulatory peritoneal dialysis. In the equipment for continuous ambulatory dialysis, it is only natural to concede that all the tubes used therein are always subject to external forces such as tension, compression, and moment. In accordance with this invention, since the union of two connector members is locked without imparting any twist to the tubes, the possibility that the union of the connector member will be spontaneously broken without being perceived by the patient is unthinkable. In the case of a connector which joins two tubes through simple mutual insertion of connector members because of absence of a locking mechanism or in the case of a connector which, although provided with a locking mechanism, inevitably imparts a twist to the tubes at the time that union of the tubes is locked, the possibility of the union of tubes being spontaneously broken is quite strong. For the safety of the patient, this possibility must be precluded at all cost. In the latter case, the locking of the union of tubes should be performed very strongly to ensure the safety mentioned above. The patient, however, may find it difficult to undo such strong union. According to this invention, the medical treatment to be administered and the equipment to be used therefore both gain greatly in reliability.

As another embodiment of this invention, the retaining members 15 may be formed of a heat shrinkable tube such as a heat shrinkable silicone tube and these members may be forcibly wrapped around the outer surface of the joining of the tubes attached by insertion to the connectors. At the same time, the tubes of silicone resin can be attached quite powerfully to the connector members owing to the squeezing action of the supporting members by heating such as steam autoclaving sterilization and the like. Otherwise, the supporting members may be formed of fluorine resin or cork and they may be wrapped directly around the connector members or indirectly around the fastened ends of tubes which in turn are wrapped around the connector members. Since fluorine resin possesses virtually no elasticity and cork possesses only low tensile strength despite its good elasticity, such supporting members can be attached in a highly desirable condition.

As yet another embodiment of this invention, the connector members may be designed so as to be mutually joined by means of matched converging and diverging tubular surfaces or annular sealing members such as O rings and countersunk packings instead of mutual insertion or end-face contact. These connector members provide a union of more reliable water tightness. In another embodiment of this invention, union of one male connector member and one female connector member can be secured in a wide variety of constructions which warrant perfect union by straight mutual insertion.

What is claimed is:

1. A method of connecting connector members associated with medically therapeutic tubes to be joined to one another, while providing flame sterilization, thereby preventing microorganic invasion into the interior of the tubes through the connector members, comprising:

providing a tubular male connector member made of a thermally resistant and corrosionproof material, said male connector member having a tubing end adapted to be connected to a therapeutic tube;

selecting the material of said male connector member also to be flame-resistant and flame-sterilizable;

inserting said tubing end of the male connector member liquid-tightly into an end of a first therapeutic tube;

providing a tubular female connector member made of a thermally resistant and corrosionproof material, said female connector member having a tubing end adapted to be connected to a therapeutic tube;

selecting the material of said female connector member also to be flame-resistaat and flame-sterilizable;

inserting said tubing end of the female connector member liquid-tightly into an end of said second therapeutic tube;

said male and female connector members being mutually engageable to connect said first and second therapeutic tubes together;

providing a locking mechanism on the male and the female connector members for locking the male and female connector members liquid-tightly to one another when placed in an engaged state;

flame sterilizing at least one of the male and female connector members by directing a flame thereat, thereby sterilizing at least the area which is contacted by the flame;

engaging the male and the female connector members with one another without relative twisting movement during said flame sterilizing step; and actuating the locking mechanism on the connector members to lock the male and female connector members together after said flame sterilizing and engaging steps, thereby preventing microorganic invasion into the interior of said first and second therapeutic tubes through the connector members.

2. The method of claim 1, including retaining the associated ends of said first and second therapeutic tubes on the tubing ends of the male and the female connector members during said flame sterilizing step by placing retaining members about the respective ends of the therapeutic tubes.

3. The method of claim 2, including heat-shrinking each of the retaining members, thereby securing said associated tube ends to the tubing ends of the connector member bodies.

4. The method of claim 1, wherein said flame sterilizing step is carried out by holding at least one of the connector members in the flame of an alcohol lamp.

5. The method of claim 1, wherein at least one of said therapeutic tubes is made of plastic material.

6. The method of claim 1, wherein at least one of said therapeutic tubes is made of rubber material.

7. The method of claim 1, wherein said flame sterilizing step comprises flame sterilizing those portions of said male and female connector members which are connected together during said engaging step.

8. The method of claim 1, wherein said flame sterilizing step comprises sterilizing both of said male and female connectors prior and during said engaging step.

9. The method of claim 1, wherein said flame sterilizing step comprises directing a sterilizing flame away from said therapeutic tubes such that said flame does not contact said therapeutic tubes.

10. The method of claim 1, wherein said therapeutic tubes and connector members comprise at least a part of a peritoneal dialysis system.

11. The method of claim 1, wherein at least one of said therapeutic tubes is connected to a body of a patient.

12. The method of claim 11, wherein said therapeutic tubes and connector members comprise at least a part of a peritoneal dialysis system.

* * * * *